United States Patent [19]
Fischell

[11] Patent Number: 5,127,902
[45] Date of Patent: Jul. 7, 1992

[54] APPARATUS AND METHOD FOR PRECISELY CONTROLLING THE EXCISION OF OBSTRUCTIVE TISSUE IN A HUMAN BLOOD VESSEL

[75] Inventor: Robert E. Fischell, Dayton, Md.

[73] Assignee: Medical Innovative Technologies R&D Limited Partnership, Dayton, Md.

[21] Appl. No.: 577,633

[22] Filed: Sep. 5, 1990

[51] Int. Cl.⁵ .............................................. A61B 17/20
[52] U.S. Cl. ....................................... 604/22; 604/53; 606/159
[58] Field of Search .................... 604/19, 20, 22, 49, 604/52, 53; 128/751, 898; 606/159

[56] References Cited

U.S. PATENT DOCUMENTS

| | | | |
|---|---|---|---|
| 4,765,332 | 8/1988 | Fischell et al. | 606/159 |
| 4,886,061 | 12/1989 | Fischell et al. | 604/22 |
| 4,898,575 | 2/1990 | Fischell et al. | 604/22 |
| 5,011,490 | 4/1991 | Fischell et al. | 604/22 |
| 5,030,201 | 7/1991 | Palestiant | 604/53 |

Primary Examiner—Stephen C. Pellegrino
Assistant Examiner—Michael Rafa

[57] ABSTRACT

A means and method is described that uses a tissue excision (atherectomy) catheter system for creating a passageway through obstructive tissue in a blood vessel of a human body such that the passageway has a greater luminal diameter than the outside diameter of a percutaneously inserted catheter used to create that passageway. A guide wire is first percutaneously inserted into the blood vessel and advanced through the obstructive tissue. A percutanesouly inserted catheter is then advanced over the guide wire and it cuts through the obstructive tissue while the blood vessel is compressed at the site of the obstructive tissue by means of an externally applied pressure cuff. The compressional force on the blood vessel is then released and the catheter and guide wire are removed from the blood vessel. This procedure results in a luminal diameter of the passageway cut in the obstructive tissue that is larger than the outside diameter of the tissue excision catheter.

23 Claims, 6 Drawing Sheets

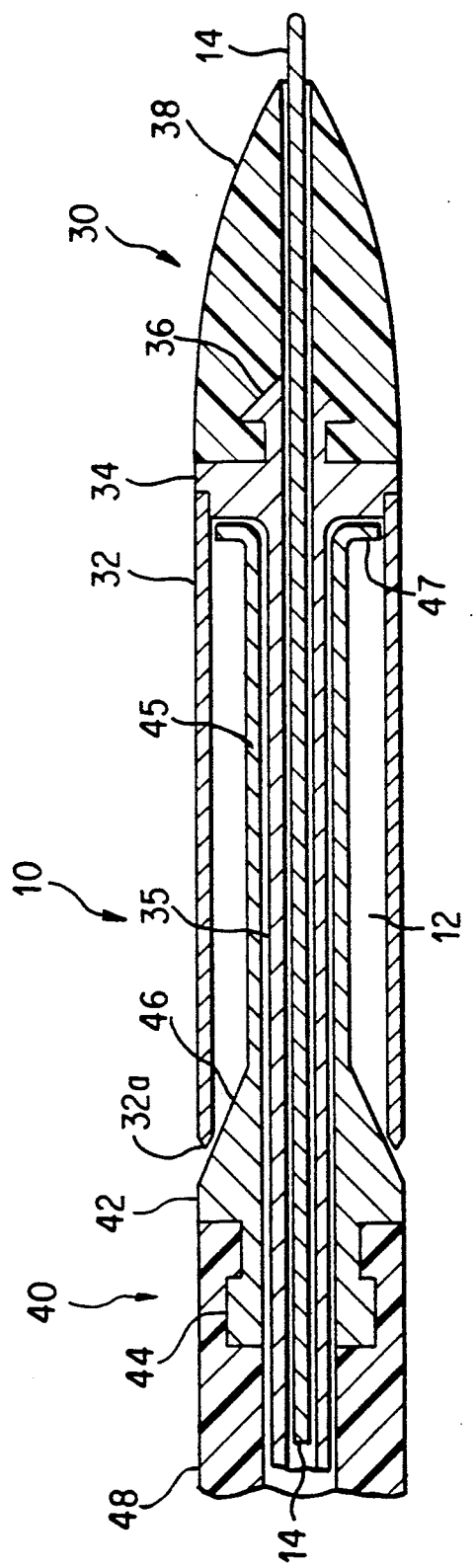
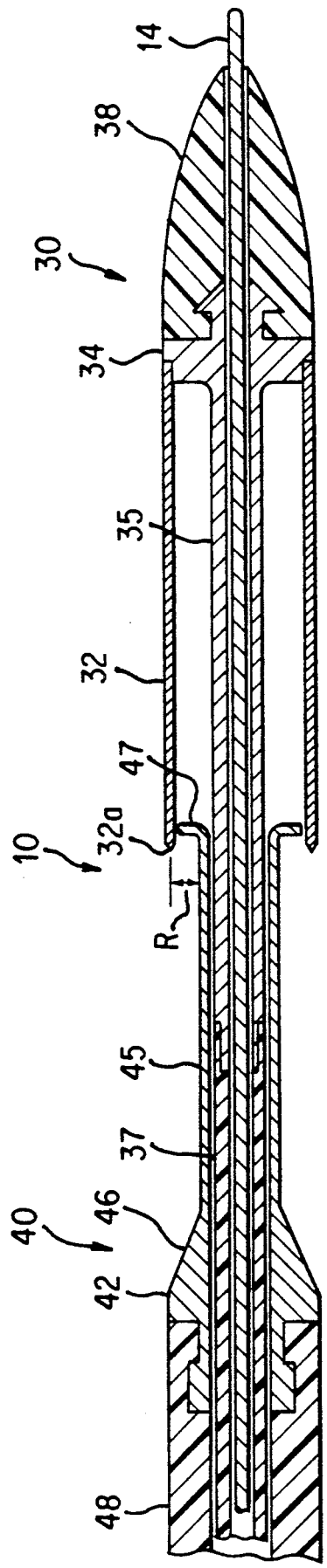
FIG. 1
FIG. 2

APPARATUS AND METHOD FOR PRECISELY CONTROLLING THE EXCISION OF OBSTRUCTIVE TISSUE IN A HUMAN BLOOD VESSEL

BACKGROUND OF THE INVENTION

1. Field of the Invention

This invention constitutes a means and method for the excision of tissue from within the lumen of a human blood vessel by the use of a Precision Atherectomy Catheter (PAC) system. Although much of the description herein concerns atherectomy of plaque from within an artery, this invention is more generally applicable to the excision of any tissue from any blood vessel of a human body.

2. Description of the Prior Art

There are numerous treatments to remove tissue from lumens within the vessels in a human body including surgical interventions such as endarterectomy and by-pass surgery using veins or artificial graft materials. Balloon angioplasty is becoming increasingly popular for the dilation of arterial stenoses without the excision of the plaque. More recently atherectomy, the excision from an artery of atheromatous plaque, has been successfully used to open arterial stenoses.

In UK Patent Application GB-A 2,044,103 by D. N. Ross dated Oct. 15, 1980 there is described a device for removing plaque within an artery by drawing together two cutting edges that are initially placed on either side of an arterial stenosis. One significant disadvantage of the Ross invention is that it cannot cut a passageway through the plaque that is larger than the outside diameter of the catheter.

U.S Pat. No. 4,765,332, issued Aug. 23, 1988 to Robert E. and Tim A. Fischell, entitled "Pullback Atherectomy Catheter System," teaches a retrograde cutting catheter that can be advanced over a guide wire with a single cutting edge that can be rotated or mechanically vibrated, but does not teach a means for forming a passageway through the plaque that is larger than the outside diameter of the catheter.

U.S. patent application Ser. No. 447,187 filed on Dec. 7, 1989 by Robert E, Fischell and Tim A. Fischell (which is included herein by reference) describes an atherectomy catheter which also is incapable of forming a passageway though a blood vessel that is larger than the outside diameter of that catheter.

The European Patent Application No.EP-A 0 163,502 filed on May 5, 1985 by J. B. Simpson describes an atherectomy catheter which can form a passageway through an arterial stenosis that is larger than the outside diameter of the catheter. This is accomplished by inflating a balloon opposite a window in a housing at the catheter's distal end and pushing a cutter through the plaque and then pushing the plaque forward into a plaque collection chamber. The window is then rotated to a new position in the plaque and the process is repeated several times until a passageway is formed that is a larger diameter than the catheter's outer diameter when the balloon is not inflated. Although the Simpson invention does solve the problem of opening a passageway in the artery that is larger than the outside diameter of the catheter when the balloon in not inflated, there is no control over the thickness of plaque that is removed with each pass of the cutter. Thus at a low pressure in the balloon very little plaque would enter the window and therefore very little plaque would be removed. At a very high balloon pressure, much more plaque would be pushed into the window and therefore there would be a much deeper cut into the plaque and considerably more plaque would be removed (as compared to low pressure) and in fact the arterial wall could be (and in practice has been) perforated. Furthermore, for the same balloon pressures, harder plaque would not enter the window as much as softer plaque, and in that case, less plaque would be removed by the cutter. In summary, with the Simpson atherectomy catheter, the amount of plaque removed on each forward thrust of the cutter is indeterminate and arterial perforation does occur.

SUMMARY OF THE INVENTION

The Precision Atherectomy Catheter (PAC) system as described herein is designed to overcome many of the shortcomings of the prior art devices. The PAC system as described herein is applicable only to blood vessels in parts of the human body which can be compressed; e.g., the arteries in the arms, legs, neck or abdomen.

PAC uses a pressure cuff surrounding the portion of the body at the site of the tissue obstruction to compress the tissue as the atherectomy catheter moves through and cuts that tissue. After the atherectomy is completed, the pressure cuff is returned to ambient pressure and the catheter is removed. The pressure of blood in the artery or vein then moves the wall of the blood vessel outward so that the passageway formed is in fact a larger diameter than the catheter's outside diameter.

An additional characteristic of the PAC design is that the obstructive tissue (typically plaque) is always cut off the vessel wall by an exact amount. Since modern angiography provides an indication of plaque thickness on the wall, by limiting the plaque thickness that can be removed on a single pass of PAC through that tissue, the PAC system can provide assurance that the vessel wall will not be perforated.

Since there are now ultrasonic imaging catheters that provide precise measurement of plaque thickness on an arterial wall, this ultrasonic imaging can now be used in conjunction with the PAC system to provide further safety by preventing perforation of the arterial wall.

Thus one objective of the PAC system is to make a passageway through obstructive tissue in a human blood vessel that is larger than the outside diameter of the catheter.

Another objective of the PAC system is to measure the thickness of the obstructive tissue on the blood vessel wall and to use compression combined with a specific cutter configuration to excise not more than that known thickness of obstructive material from the wall of the blood vessel.

Still another objective of the PAC system is to easily remove the plaque collected in the plaque collection chamber.

BRIEF DESCRIPTION OF THE DRAWINGS

FIG. 1 is a longitudinal cross section of the distal end of the catheter subsystem of the PAC system shown in its closed position.

FIG. 2 is a longitudinal cross section of the distal end of the catheter subsystem of the PAC system shown in its open position.

DETAILED DESCRIPTION OF THE DRAWINGS

Figure 3:
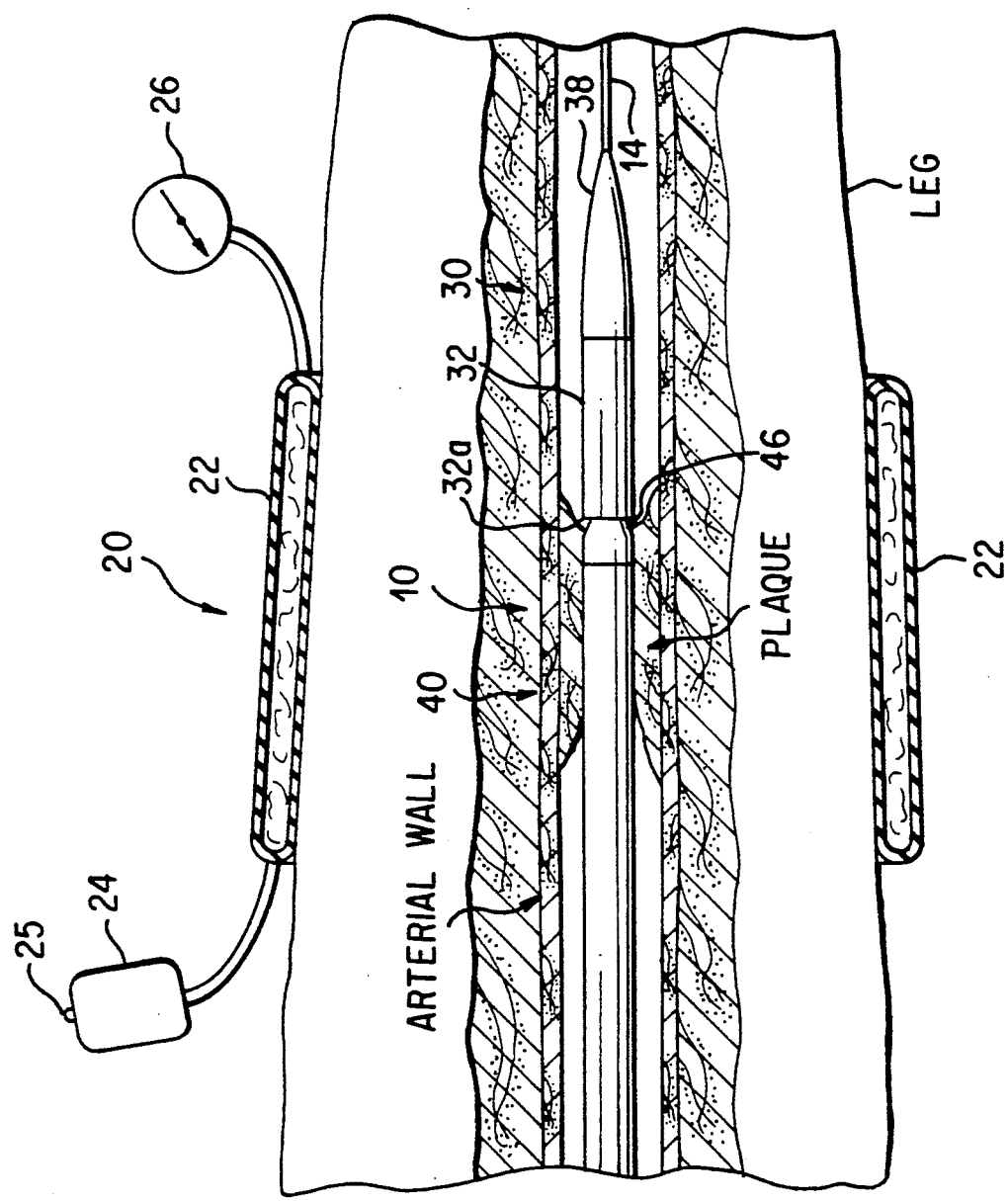
FIG. 3 illustrates the catheter subsystem and the pressure cuff subsystem of the PAC system with the catheter subsystem shown lying in its closed position within a stenosis in an artery of a leg and with the pressure cuff uninflated.

The Precision Atherectomy Catheter (PAC) system consists of two major subsystems: the catheter subsystem and the pressure cuff subsystem. FIG. 1 is a longitudinal cross-sectional view showing the distal end of the catheter subsystem 10 in the closed position. The catheter subsystem 10 consists of 3 principal parts: the guide wire 14, the cut/collect catheter 30 and the closing catheter 40. From FIG. 1 we see that the cut/collect catheter 30 has a cutting cylinder 32 which has a sharpened edge 32a at its proximal end and at its distal end it is joined (typically welded) to the central support 34. At the distal end of the central support 34 is a distal projection 36 which is designed to hold onto an elastomer, flexible tip 38. When the flexible tip 38 is molded onto the distal projection 36, a releasing agent is first applied to the distal projection 36 so that after the molding process, the flexible tip 38 is free to rotate about the distal projection 36 of the central support 34. In the proximal direction, the central support 34 has a central cylinder 35 which surrounds the guide wire 14.

Figure 7:
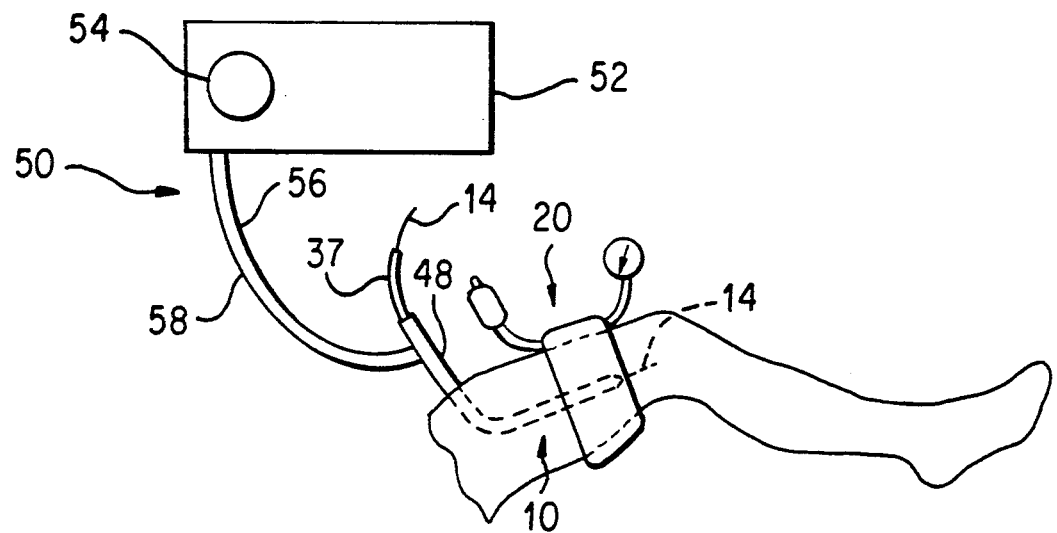
FIG. 7 shows the PAC system in conjunction with an endoluminal ultrasonic imaging system being used for atherectomy in a human leg.

The closing catheter 40 consists of a distal cylinder 45 which has a flared end 47 at is distal end and at its proximal end is connected to a cone 46 which is connected to the straight section 42 of the metal distal portion of the closing catheter 40. The section 42 also has a proximal projection 44 designed to securely hold onto a plastic cylinder 48. At its proximal end (which is shown in FIG. 7), the plastic cylinder 48 of the closing catheter 40 extends outside the patient's body.

Located between the outer surface of the distal cylinder 45 and inner surface of the cutting cylinder 32 is the plaque collection chamber 12. When the atherectomy procedure is completed, the catheter subsystem 30 will be in the closed condition as shown in FIG. 1, and the plaque that is to be cut and collected will lie within the plaque collection chamber 12.

FIG. 2 shows a longitudinal cross-sectional view of the distal end of the catheter subsystem 10 of the PAC system with the catheter subsystem 10 shown in the open position. The open position is achieved by pulling the closing catheter 40 backwards (i.e., in a retrograde direction) relative to the cut/collect catheter 30 whose proximal end also extends outside the body. FIG. 2 shows a plastic cylinder 37 attached to the central cylinder 35 of the central support 34 of the cut/collect catheter 30. It is this plastic cylinder 37 of the cut/collect catheter that extends proximally outside the patient's body as shown in FIG. 7. Only when starting from its open position, as shown in FIG. 2, is the catheter subsystem 10 capable of excising plaque from the walls of a human blood vessel.

One thing to note in FIG. 2 is the radial distance between the outer cylindrical surface of the distal cylinder 45 and the cutting edge 32a of the cutting cylinder 32 It is this radial offset distance R which determines the precise thickness of obstructive tissue that is cut off as the cut/collect catheter 30 is pulled back in a retrograde direction over the tissue while the closing catheter 40 remains stationary.

At its proximal end, lying outside the patient's body, the plastic cylinder 37 is typically connected to a rotating device such as is described in U.S. patent application Ser. No. 447,187 by Robert E. and Tim A. Fischell. This rotating device is used to spin the cutting edge 32a as it is pulled back through the plaque to be excised thus enhancing the cutting action.

The cutting cylinder 32 of the cut/collect catheter 30 is typically fabricated from a hardenable, 400 series stainless steel. All other metal parts would typically be made from 304 stainless steel or a metal with equivalent characteristics. All plastic parts would typically be made from elastomer materials such as polyethylene, polyurethane, Nylon or equivalent plastic materials. The outer diameter of the catheter subsystem would typically lie between 1.0 and 5.0 mm.

FIG. 3 shows the entire PAC system which consists of the catheter subsystem 10 and pressure cuff subsystem 20. It should be remembered that the catheter subsystem 10 consists of a guide wire 14, a cut/collect catheter 30 and a closing catheter 40. The pressure cuff subsystem 20 consists of an inflatable cuff 22, a pumping means 24 with a pressure relief valve 25 and a pressure gauge 26 all of which are illustrated in FIG. 3.

To achieve the condition shown in FIG. 3, it is typical to have an insertion sheath inserted at the groin of a patient. After the insertion sheath is in place, a guide wire is advanced through the sheath and through the stenosis consisting of plaque located somewhere in an artery or a vein. FIG. 3 illustrates plaque forming a stenosis of an artery in the leg. After the guide wire is placed through the stenosis, the catheter subsystem 10 having a tapered distal end flexible tip 38 is advanced over the guide wire 14 and through the stenosis until the cutting edge 32a of the cutting cylinder 32 lies just distal to the stenosis. To accomplish this positioning within the stenosis, the catheter subsystem 10 is advanced in the closed position; i.e., with the cone 46 of the closing catheter 40 pushed against the proximal end of the cutting cylinder 32.

Figure 4:
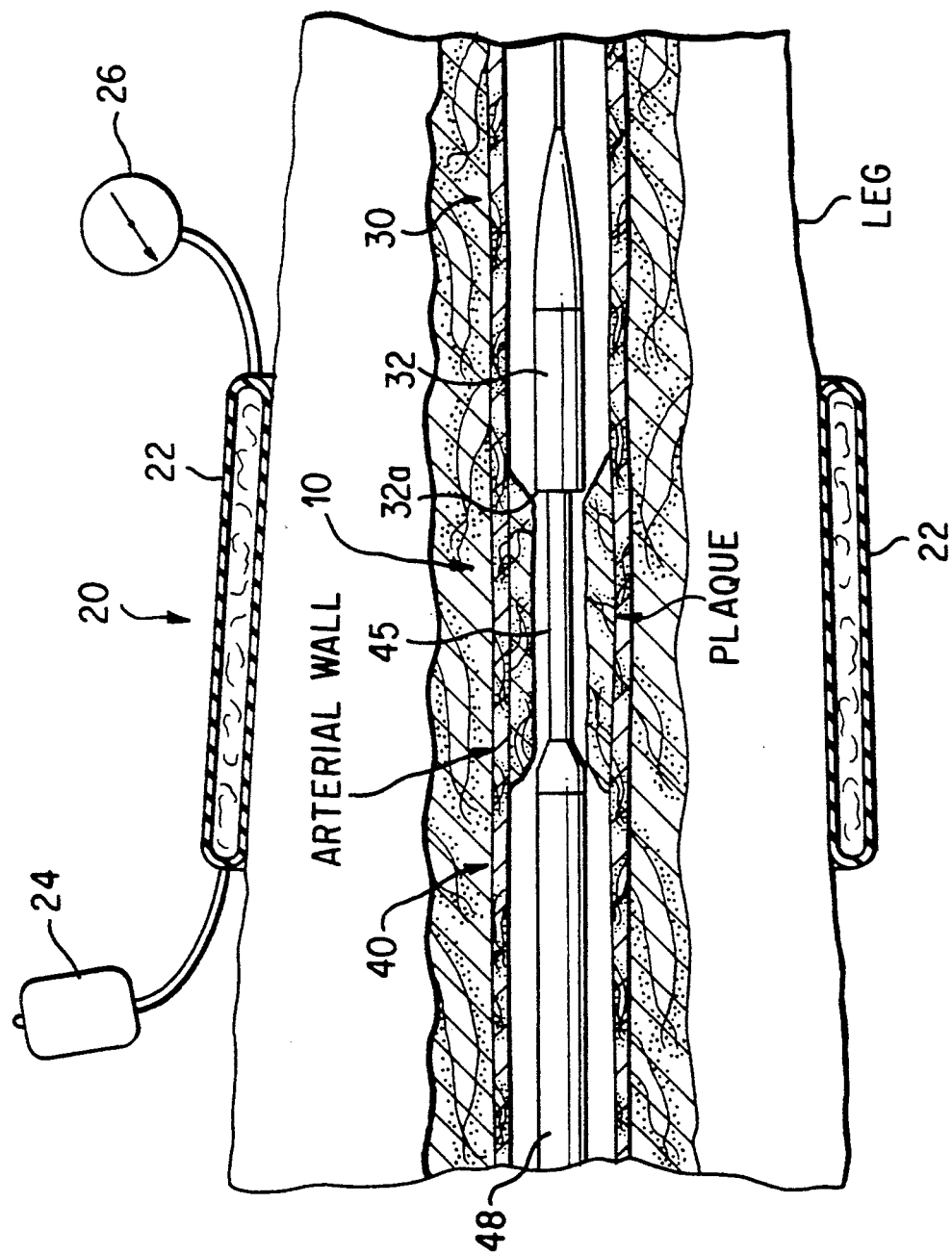
FIG. 4 illustrates the PAC system with the catheter subsystem shown in the open position within a leg artery and with the pressure cuff uninflated.

The next step in this procedure (as shown in FIG. 4) is to pull back on the plastic cylinder 48 that lies outside the body which causes the closing catheter 40 to be pulled back while keeping the cut/collect catheter 30 stationary. Pulling the closing catheter 40 back exposes the cylinder 45 at the distal end of the closing catheter 40 and the cutting edge 32a of the cutting cylinder 32. Also, as can be seen in FIG. 4, the inside diameter of the lumen in the plaque would typically remain at the same diameter as the outside diameter of the catheter subsystem 10. This is because plaque is a reasonably plastic material and will remain at essentially that same diameter (or slightly less) to which it was dilated by the insertion of the catheter subsystem 10 as shown in FIG. 3. One can also see in FIG. 4 that the pressure cuff subsystem 20 remains in the uninflated condition.

Figure 5:
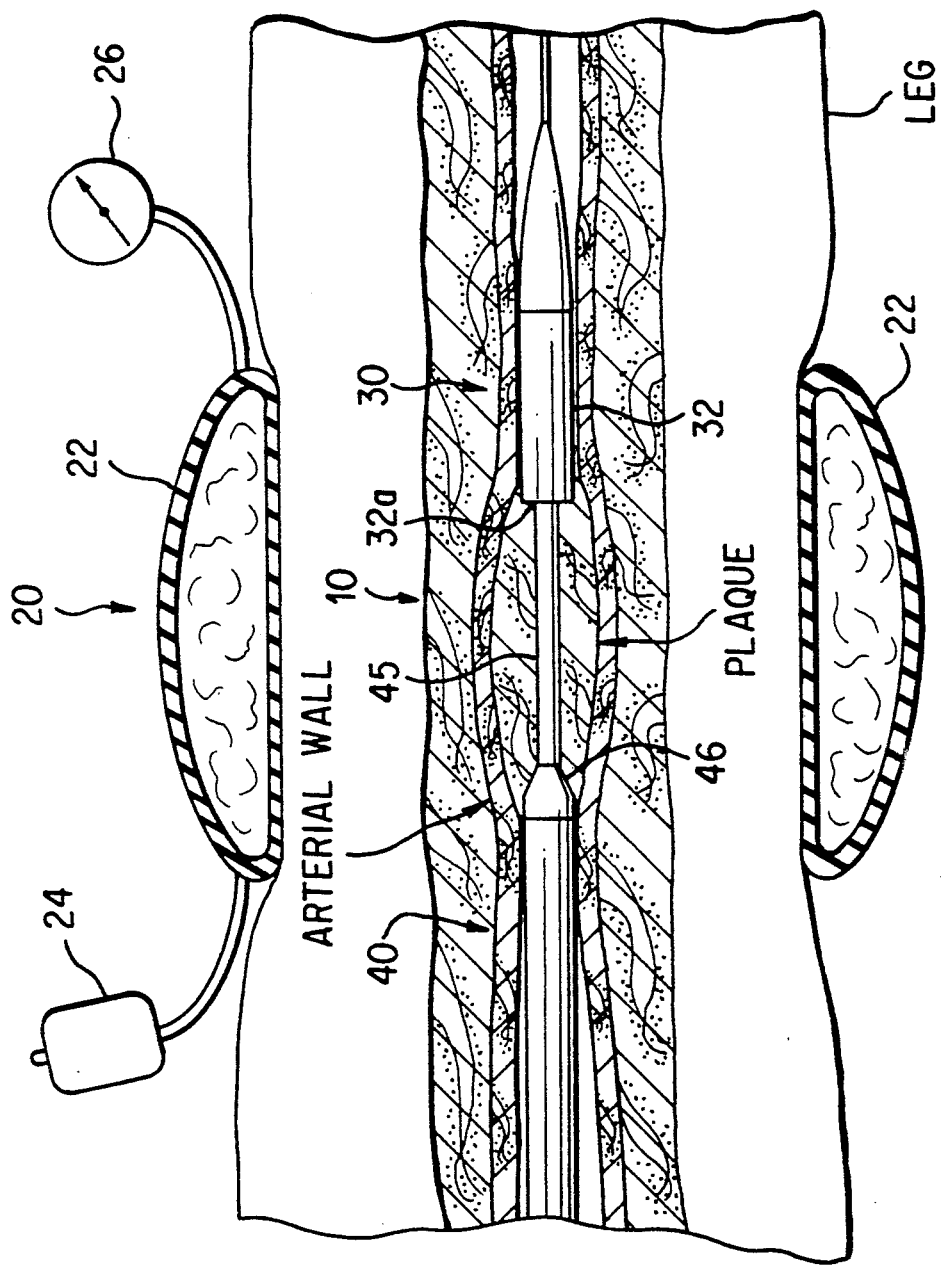
FIG. 5 illustrates the PAC system with the distal end of the catheter subsystem shown in its open position and with the pressure cuff inflated so as to compress the plaque against the closing catheter's distal cylinder.

FIG. 5 shows the next step in this procedure wherein the inflatable cuff 22 of the pressure cuff subsystem 20 is inflated to a higher pressure. This inflation can be accomplished by pumping on a pressure bulb 24 as typically accomplished when measuring blood pressure. The exact level of the pressure attained will be indicated by the pressure gauge 26. When the inflatable cuff 22 is inflated as indicated by the pressure guage 26, the effect is to collapse the arterial wall around the outer diameter of the catheter subsystem 10, and more importantly the plaque is pushed onto the outer cylindrical surface of the distal cylinder 45 of the closing catheter 40. In this position a precise thickness of plaque is ready to be excised. Specifically, the precise plaque thickness to be excised is the equal to the radial offset R as shown in FIG. 2.

With the inflatable cuff 22 inflated to a reasonably high pressure, the cut/collect catheter 30 is pulled backwards so that the cutting edge 32a of the cutting cylinder 32, typically while rotating, is pulled back through the plaque thus cutting a precice thickness of plaque away from the remaining plaque which adheres to the arterial wall. The pullback of the cut/collect catheter 30 continues until the proximal end of the cutting cylinder 32 is in contact with the cone 46 of the closing catheter 40. After this cutting has been completed, all the excised plaque will be situated in the plaque collection chamber 12 (see FIG. 1).

Figure 6:
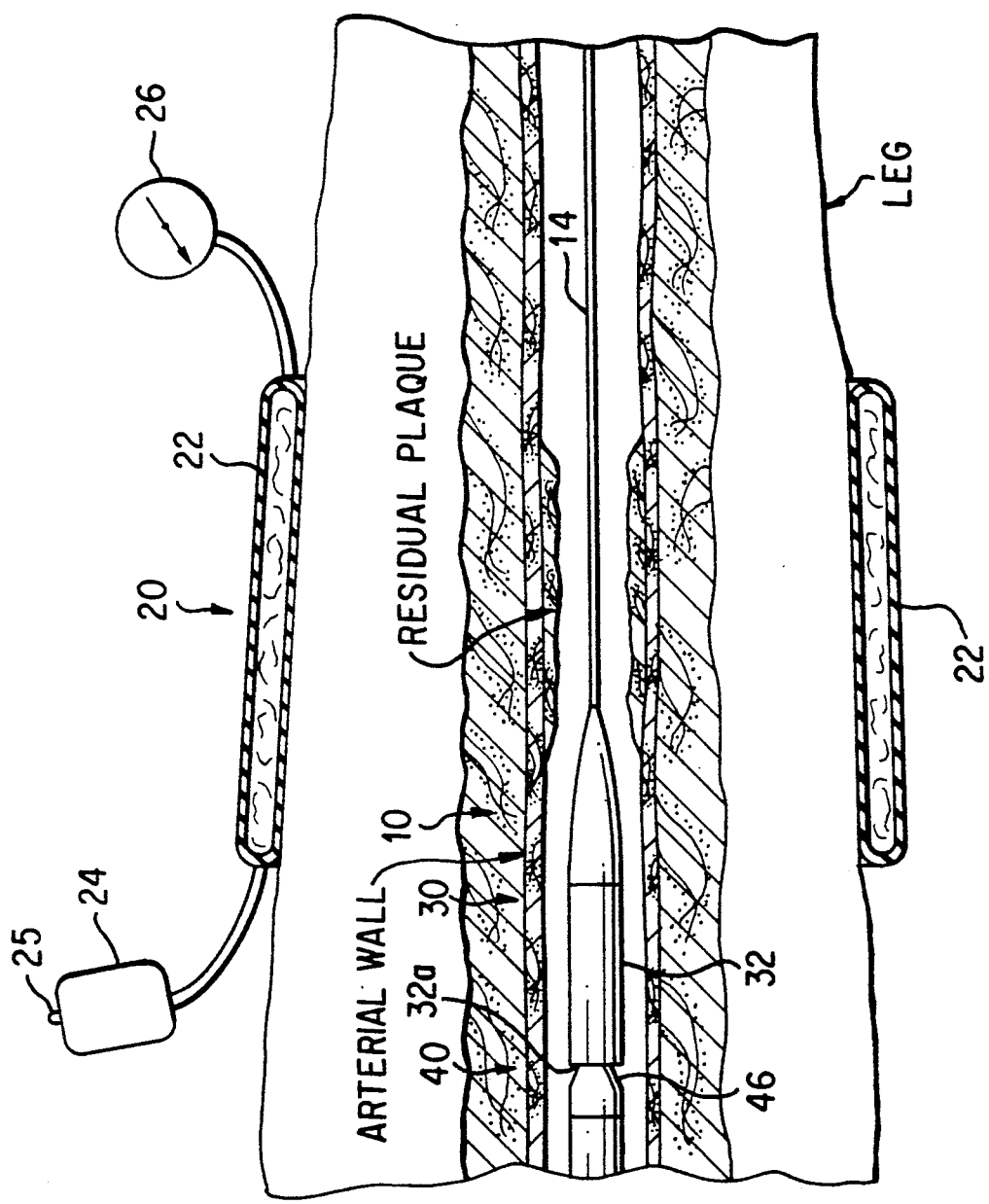
FIG. 6 shows the PAC system with the catheter subsystem pulled back and closed and the pressure cuff deflated.

FIG. 6 illustrates the next step in using the PETEC system. Specifically FIG. 6 shows that the pressure cuff subsystem 20 has been deflated. This can be accomplished by opening a valve 25 on the pumping means 24 the pressure being indicated by the pressure guage 26. Such valves are typically found on pressure cuffs used to measure blood pressure. We also see in FIG. 6 that the proximal end of the cutting cylinder 32 is placed tightly against the cone 46 of the closing catheter 40. In FIG. 6, the entire catheter subsystem 10 (except the guide wire 14) has been pulled back beyond the residual plaque of the stenosis. Because the artery can expand after the inflatable cuff 22 is deflated, the luminal diameter inside the residual plaque will be a larger diameter than the outside diameter of the catheter subsystem 10. This is a most important objective in the field of atherectomy, in that, the ideal atherectomy system will remove plaque from the arterial wall to a larger luminal diameter than the outside diameter of the catheter used to perform the procedure. By this method, comparatively small catheters can be percutaneously placed through the patient's skin and yet the catheter can accomplish the function of removing plaque from the blood vessel to a comparatively large diameter. The method described herein can therefore be used to leave only a small residual of obstructive tissue on the wall of the blood vessel.

After the cutting has been achieved and the amount of plaque adhering to the wall significantly reduced, the entire catheter subsystem 10 is removed from the body. When the catheter subsystem 10 is outside the body, the closing catheter 40 is pulled back from the cut/collect catheter 30. The process of opening the distal end of the catheter subsystem 10 results in the flared end 47 on the distal cylinder 45 sweeping out all the plaque contained in the plaque collection chamber 12 (see FIGS. 1 and 2). Because the outer edge of the flared end 47 fits closely within the inside surface of the cutting cylinder 32, all the plaque captured in the plaque collection chamber 12 will be automatically pulled out of the plaque collection chamber 12 when the closing catheter 40 is pulled back. The plaque thus removed can undergo pathologic examination to determine the nature of the excised tissue.

Although the procedure described herein uses a pressurized cuff set at a comparatively high pressure when the cut/collect catheter 30 is pulled back through the plaque, alternative methods of using such a pressure cuff subsystem are available. For example, it may be desirable to pressurize the inflatable cuff 22 to a considerably higher pressure when the distal end of the catheter subsystem 10 has been opened. However, in contradistinction to the aforementioned method, the inflatable cuff 20 could be deflated just prior to pulling back the cutting edge 32a of the cutting cylinder 32 through the plaque. This method could be effective because the plaque is comparatively plastic and the mere application of pressure on the arterial wall can push the plaque against the cylinder 45 so that, even when the pressure is relieved there will be a considerable amount of plaque in contact with the outer cylindrical surface of the distal cylinder 45. The plaque would be excised when the cutting cylinder 32 is pulled back until its proximal end is in contact with the cone 46 at the distal end of the closing catheter 40. One reason why this method might be preferred is that it would tend to avoid perforation of the normal arterial wall. This method would provide cutting of only that obstructive tissue which extends inwardly from the wall of the blood vessel and not the blood vessel wall itself.

Typical pressures that would be used for the procedure illustrated in FIGS. 3, 4, 5 and 6 would be just above the patient's systolic pressure. For example, if the patient's systolic pressure in his leg was measured to be 150 mm of Hg, it would be useful to use pressures that are 0 to 50 mm of Hg above this pressure. However pressures between 50 and 250 mm Hg may be successfully used for this procedure. When the technique of pressurizing the cuff and deflating the cuff just prior to pulling back the cutting cylinder 32 of the cut/collect catheter 30 is used, one might go to pressures as high as 300 mm of Hg so that one can be sure that the plaque has been plastically deformed onto the outer surface of the distal cylinder 45 of the closing catheter 40.

Although one might conceive of a simple belt being used in place of the pressure cuff subsystem 20, without an accurate method for measuring the compressional force on the delicate blood vessel, damage to the vessel including perforation may be the result. Thus, a rather precise indication of compressional pressure on the blood vessel is essential in order to achieve a consistently safe atherectomy procedure.

It should be understood that throughout the description of the PETEC system given above, the thickness of the obstructive tissue on the vessel wall is measured by angiography prior to tissue excision. Since this tissue thickness can be determined before cutting and since the precise thickness of tissue removed (as given by the radial offset R) is known, the risk of vessel wall perforation is minimized.

It is conceived that catheter subsystems with varying offsets may be used depending on the measured thickness of obstructive tissue to be excised from the vessel wall. Typical dimensions for the radial offset R would be between 0.1 and 1.0 mm. For example, if a tissue thickness on the vessel wall is measured by angiography to be 0.7 mm, then a catheter subsystem with R = 0.5 mm might be used to excise a plaque thickness of 0.5 mm. This would open a vessel to a sufficiently large diameter while avoiding the risk of perforating the vessel wall.

Another method for measuring tissue thickness on the wall is by ultrasonic imaging. Specifically U.S. Pat. No. 4,917,097 entitled "Apparatus and Method for Imaging Small Cavities," which is incorporated herein by reference, describes a system which is capable of measuring the thickness of tissue on the vessel wall to 0.1 mm. A separate catheter with this measurement capability could be used to measure obstructive tissue wall thickness prior to using the PETEC system for excising tissue. It is further conceived that the closing catheter 40 could be used as a sonography catheter to measure the thickness of obstructive tissue. Specifically, FIG. 7 shows the pressure cuff subsystem 20 wrapped around a human leg into which the catheter subsystem 10 has been percutaneously advanced over a guide wire 14. The guide wire 14, the plastic cylinder 48 of the closing catheter 40 (see FIGS. 1 and 2) and the plastic cylinder 37 of the cut/collect catheter 30 (see FIG. 2) are all shown extending proximally outside of the patient's body. An endoluminal sonography system 50 is also shown in FIG. 7. This system 50 consists of electronic equipment 52 which is used to generate ultrasonic signals and to measure the reflected signal from within the blood vessel. The equipment 52 typically includes a CRT display 54. Electrical wires 56 and 58 are shown connecting into the plastic cylinder 48 of the closing catheter 40. Although only two wires are shown, additional wires may be required to obtain detailed ultrasonic imaging of the vessel wall.

Figure 8:
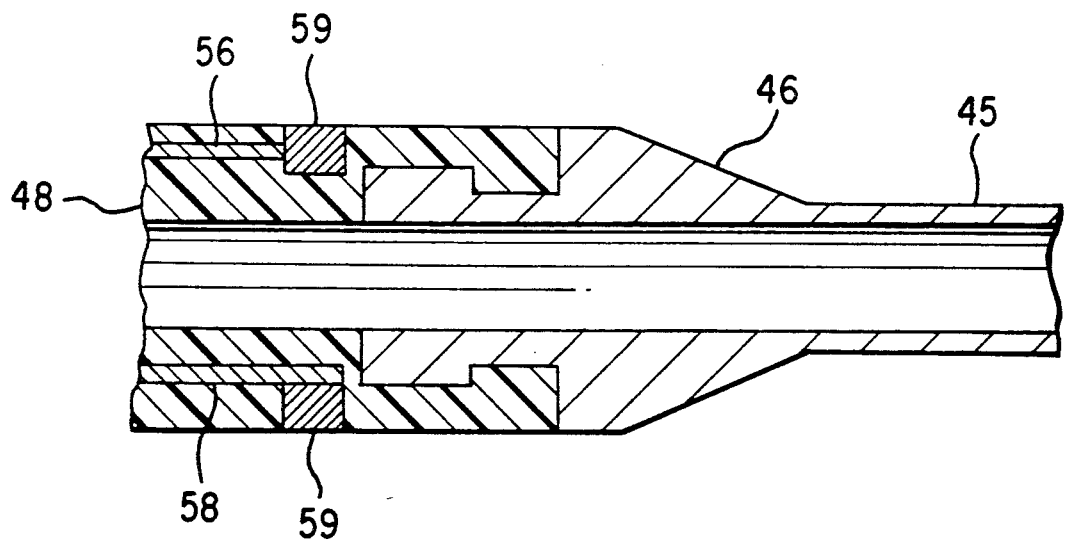
FIG. 8 is a cross-sectional view showing an ultrasonic transducer placed near the distal end of the closing catheter of PAC's catheter subsystem.

FIG. 8 shows the distal end of the wires 56 and 58 as they are connected into an ultrasonic transducer 59 that is placed at the distal end of the plastic tube 48. The technique for obtaining endoluminal images of blood vessels is well known in the art and will not be described in any more detail herein.

Using the system illustrated in FIGS. 7 and 8, it is possible to precisely measure the thickness of obstructive tissue on the blood vessel wall. This measurement can be accomplished with a separate catheter or with the addition of sensing means at the distal end of the closing catheter as shown in FIG. 8. When combined with the PETEC's capability to excise a precise thickness of obstructive tissue, the ultrasonic imaging system provides an excellent combined system for precisely excising such tissue and obtaining the maximum luminal opening with the least risk of vessel wall perforation.

Although the discussion herein is principally concerned with a catheter that cuts in the retrograde direction, the invention that is taught herein is equally applicable to atherectomy catheters that cut in the anterograde direction such as that described in the Fischell et al U.S. Pat. No. 4,898,575 or the Simpson European Patent Application No. EP-A 0 163,502. Furthermore, various blade configurations such as those described in the prior art could be used in conjunction with the technique for compressing plaque as described herein. Furthermore, ablation techniques such as using grinding, laser vaporization or high energy ultrasonic vibrators could be used successfully with the tissue compression methodology described herein.

Various other modifications, adaptations, and alternative designs are, of course possible in light of the above teachings. Therefore, it should be understood at this time that within the scope of the appended claims, the invention may be practiced otherwise than as specifically described herein.

What is claimed is:

1. A precision atherectomy catheter system for creating a passageway through obstructive tissue in a blood vessel of a human body such that the passageway has a greater luminal diameter than the outside diameter of a percutaneously inserted catheter used to create that passageway comprising;
    a guide wire adapted to be percutaneously inserted into the blood vessel and advanced through the obstructive tissue,
    a percutaneously inserted catheter adapted to be advanced over said guide wire and having a cutting means located at a distal portion of the catheter, said cutting means being adapted to cut through said obstructive tissue when the blood vessel is being compressed; and
    a means for compressing the blood vessel when said catheter is being moved through said obstructive tissue.

2. The system of claim 1 wherein said means for compressing the blood vessel is an inflatable cuff that surrounds that portion of the human body through which the blood vessel passes, said inflatable cuff being adapted to provide a first and higher pressure when said catheter is cutting said obstructive tissue and a second and lower pressure after said obstructive tissue has been cut.

3. The system of claim 2 wherein the inflatable cuff includes pumping means and pressure releasing means to alter the pressure in said cuff during the tissue excision procedure.

4. The system of claim 2 wherein the inflatable cuff includes means for measuring the pressure within the cuff.

5. The system of claim 2 wherein said first and higher pressure is set between 50 and 250 mm of Hg.

6. A precision atherectomy catheter system for creating a passageway through obstructive tissue in a blood vessel of a human body such that the passageway has a greater luminal diameter than the outside diameter of a percutaneously inserted catheter used to create that passageway comprising;
    a percutaneously inserted catheter having means located at a distal portion of the catheter for cutting and collecting the obstructive tissue so as to excise the obstructive tissue from a blood vessel; and
    a means for compressing the blood vessel before said catheter is moved through said obstructive tissue and a means for releasing the compression of the blood vessel when said catheter is cutting through said obstructive tissue so as to excise said obstructive tissue.

7. The system of claim 6 wherein said means for compressing the blood vessel is an inflatable cuff that surrounds that portion of the human body through which the blood vessel passes, said inflatable cuff being adapted to provide a first and higher pressure before said catheter cuts said obstructive tissue and a second and lower pressure when said obstructive tissue is being cut.

8. The system of claim 7 wherein said inflatable cuff includes pumping means and pressure releasing means to alter the pressure in said cuff during the tissue excision procedure.

9. The system of claim 8 wherein said inflatable cuff includes means for measuring the pressure within the cuff.

10. A precision atherectomy catheter system for creating a passageway through obstructive tissue in a blood vessel of a human body such that the passageway has a greater luminal diameter than the outside diameter of a percutaneously inserted catheter used to create that passageway comprising:
   a guide wire adapted to be percutaneously inserted into a blood vessel and advanced through the obstructive tissue;
   a means for visualizing the thickness of said obstructive tissue on the wall of the blood vessel;
   a percutaneously inserted catheter adapted to be advanced over said guide wire and having a cutting means located at a distal portion of the catheter, said cutting means being adapted to cut through said obstructive tissue when the blood vessel is being compressed; and
   a means for compressing the blood vessel when said catheter is cutting through said obstructive tissue.

11. The system of claim 10 wherein the means for visualizing the thickness of said obstructive tissue is by angiography using contrast medium and x-ray imaging.

12. The system of claim 10 wherein the means for visualizing the thickness of said obstructive tissue is by intravascular ultrasonic imaging.

13. A precision atherectomy catheter system for removing a precise thickness of obstructive tissue off the wall of a blood vessel comprising:
   a guide wire adapted to be percutaneously inserted into a blood vessel and having its distal end beyond the obstructive tissue;
   a means for determining the wall thickness of said obstructive tissue;
   a percutaneously inserted catheter adapted to be advanced over said guide wire and further comprising a fixed and known radial offset of a cutting means relative to the radial dimension of a cylindrical surface onto which said obstructive tissue can be compressed prior to its excision using said cutting means; and
   a means for compressing said obstructive tissue onto said cylindrical surface.

14. A method for removing obstructive tissue from the wall of a human blood vessel comprising the steps of:
   percutaneously advancing a guide wire through the blood vessel until its distal end lies beyond the obstructive tissue;
   percutaneously advancing an atherectomy catheter over said guide wire:
   visualizing the thickness of obstructive tissue;
   compressing the blood vessel so as to cause obstructive tissue to be forced against the distal end of said atherectomy catheter;
   cutting through the obstructive tissue by moving a part of said atherectomy catheter which includes a tissue excising means through the obstructive tissue;
   removing the entire atherectomy catheter system from the body.

15. The method claim 14 wherein visualizing the thickness of the obstructive tissue is accomplished by angiography using a contrast medium and x-ray imaging.

16. The method of claim 14 wherein the visualizing of the thickness of the obstructive tissue is accomplished by ultrasonic imaging.

17. The method of claim 14 wherein the obstructive tissue is excised with said tissue excising means moving in a retrograde direction.

18. The method of claim 14 wherein the obstructive tissue is excised with said tissue excising means moving in the anterograde direction.

19. The method of claim 14 wherein said excising means uses a sharp cutting edge.

20. The method of claim 14 wherein said tissue excising means is an ablation means.

21. The method of claim 20 wherein said ablation means is accomplished by grinding.

22. The method of claim 20 wherein said ablation means is accomplished by using laser energy.

23. The method of claim 20 wherein said ablation means uses ultrasonic energy.

* * * * *